United States Patent [19]

Arlt et al.

[11] 4,246,199

[45] Jan. 20, 1981

[54] PROCESS FOR THE PREPARATION OF N-ALKYL-SUBSTITUTED CARBOXYLIC ACID AMIDES

[75] Inventors: Dieter Arlt, Cologne; Franz-Gerhard Behlau, Duesseldorf, both of Fed. Rep. of Germany

[73] Assignee: Bayer Aktiengesellschaft, Leverkusen, Fed. Rep. of Germany

[21] Appl. No.: 911,009

[22] Filed: May 30, 1978

[30] Foreign Application Priority Data

Jun. 8, 1977 [DE] Fed. Rep. of Germany ....... 2725889

[51] Int. Cl.$^3$ ............................................ C07C 102/08
[52] U.S. Cl. .................................. 564/124; 252/426; 203/89; 564/125; 564/130; 564/131; 564/160; 564/182; 564/204
[58] Field of Search ..................... 252/426; 260/561 R, 260/562 R, 558 R, 558 P; 203/89, DIG. 6

[56] References Cited

U.S. PATENT DOCUMENTS

| | | | |
|---|---|---|---|
| 1,934,485 | 11/1933 | Carlisle | 260/561 R |
| 1,950,875 | 3/1934 | Bond | 260/561 R |
| 2,457,660 | 12/1948 | Gresham et al. | 260/561 R |
| 2,554,846 | 5/1951 | Turinsky | 260/561 R X |
| 2,573,673 | 10/1951 | Ritter | 260/561 R |
| 2,597,446 | 5/1952 | Bruce | 260/561 R X |
| 2,601,387 | 6/1952 | Gresham et al. | 260/561 R |
| 2,628,217 | 2/1953 | Magat | 260/561 R X |
| 3,008,992 | 11/1961 | Lynn et al. | 260/561 R |
| 3,223,732 | 12/1965 | Viveen et al. | 260/561 R |
| 3,627,830 | 12/1971 | Kerber et al. | 260/561 R |
| 3,846,492 | 11/1974 | Norell | 260/561 R |
| 3,898,280 | 8/1975 | Pander | 260/561 R |
| 3,976,595 | 8/1976 | Scott et al. | 252/426 X |

FOREIGN PATENT DOCUMENTS 1198680  7/1970  United Kingdom ................ 260/561 R

OTHER PUBLICATIONS

Handbook of Chemistry and Physics, The Chemical Rubber Co., Cleveland, 49th ed., D90–D91.
Smolin, J. Org. Chem., 20(1955), pp. 295–301.

*Primary Examiner*—Arthur P. Demers
*Attorney, Agent, or Firm*—Sprung, Felfe, Horn, Lynch & Kramer

[57] ABSTRACT

An improved process for the preparation of N-alkyl-substituted carboxylic acid amides by reaction of a component which forms a carbonium ion with a nitrile, the improvement residing in carrying out the process in the presence of an acid which is inert under distillation conditions and separating the reaction mixture by distillation.

17 Claims, No Drawings

PROCESS FOR THE PREPARATION OF N-ALKYL-SUBSTITUTED CARBOXYLIC ACID AMIDES

The invention relates to a process for the preparation of N-alkyl-substituted carboxylic acid amides.

It is known to react secondary and tertiary alcohols, olefins and water, or esters with nitriles in the presence of acids, for example sulfuric acid, to give N-alkyl-substituted carboxylic acid amides (known in the literature as the Ritter reaction). For working up, the reaction mixture is treated with a large excess of water (Russian Chemical Review 29, 334 (1960)). Large amounts of dilute acids, which can only be removed at great expense, are formed in this procedure.

It is also known (German Auslegeschrift No. 2,144,230) to extract the resulting acid amide, after carrying out the reaction, by extraction with polar trisubstituted phosphoric acid esters or tetrasubstituted urea derivatives which are stable towards acid, and thus to separate it off from the acid. After the extraction, the reaction mixture is worked up in a known manner, for example by distillation.

A process has been found for the preparation of N-substituted carboxylic acid amides by reacting a component, which form a carbonium ion, with a nitrile in the presence of an acid, in which the reaction mixture is separated by distillation, the reaction being carried out in the presence of an acid which is inert under the distillation conditions.

The process according to the invention can be illustrated with the aid of the following equation:

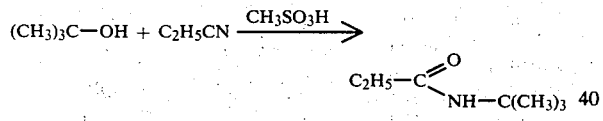

The process according to the invention is carried out in the presence of acids which are inert under the distillation conditions. Acids which can be used for the process according to the invention should form carbonium ions with components which form carbonium ions and should not lead to decomposition of the reaction mixture or of the reaction product under the distillation conditions.

Acids of the formula

wherein:

Y represents an acyl radical of an acid from the series of phosphoric acids in the 5th oxidation stage, of a phosphoric acid monoester or diester and sulphuric acid monoester, of an aliphatic or aromatic phosphonic acid, of an aliphatic or aromatic sulphonic acid or of an aliphatic carboxylic acid with a pK value of greater than 1, can preferably be employed for the process according to the invention.

Examples which may be mentioned of acyl radicals (Y) of an acid from the series of phosphoric acids in the 5th oxidation stage are the acyl radicals of orthophosphoric acid and of polyphosphoric acid.

Acyl radicals (Y) of phosphoric acid monoesters or diesters and sulphuric acid monoesters which may be mentioned are radicals of the formula

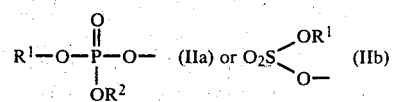

wherein:

$R^1$ and $R^2$ are identical or different and represent hydrogen or an alkyl radical with 1 to 12, preferably 1 to 8, carbon atoms.

The following phosphoric acid esters and sulphuric acid esters may be mentioned as examples: phosphoric acid dimethyl ester, phosphoric acid diethyl ester, phosphoric acid monobutyl ester, phosphoric acid di-2-ethylhexyl ester, phosphoric acid mono-n-butyl ester, sulphuric acid mono-n-butyl ester, sulphuric acid mono-(2-ethyl-hexyl) ester, sulphuric acid mono-(2-hydroxyethyl) ester and phosphoric acid mono-(2-hydroxyethyl) ester.

Further acyl radicals of phosphoric acid monoesters or diesters and sulphuric acid monoesters which may be mentioned are those in which the monoester or diester forming alcohol is a polyol, such as ethane-1,2-diol, propane-1,2-diol, 2,2-dimethylpropane-1,3-diol, trimethylolpropane and pentaerythritol.

Acyl radicals (Y) of an aliphatic or aromatic phosphonic acid which may be mentioned are radicals of the formula

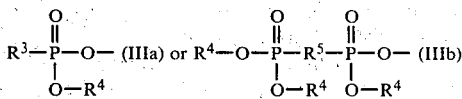

wherein:

$R^3$ represents a straight-chain or branched alkyl or alkenyl radical, preferably with 2 to 4 carbon atoms, aryl, preferably phenyl, or aralkyl, preferably benzyl, $R^4$ represents hydrogen or a straight-chain or branched alkyl radical, preferably with 1 to 4 carbon atoms, and $R^5$ represents an alkylene radical, preferably with 2 to 6 carbon atoms, which is optionally substituted by $C_1$ to $C_4$-alkyl, or an arylene radical, preferably phenylene.

The following aliphatic or aromatic phosphonic acids may be mentioned as examples: methanephosphonic acid, ethanephosphonic acid, methanephosphonic acid monomethyl ester, vinylphosphonic acid, ethane-1,2-diphosphonic acid, phenylphosphonic acid, benzylphosphonic acid and benzylphosphonic acid monomethyl ester.

Acyl radicals (Y) of an aliphatic or aromatic sulphonic acid which may be mentioned are radicals of the formula

wherein:

$R^6$ represents an alkyl radical or aralkyl radical, preferably with 1 to 18 carbon atoms, which is optionally substituted by fluorine or chlorine, or an aryl radical, preferably phenyl, which is optionally substituted by fluorine, chlorine, $C_1$-$C_4$-alkyl or a sulphonic acid group.

The following sulphonic acids may be mentioned as examples: methanesulphonic acid, ethanesulphonic acid, propanesulphonic acid, butanesulphonic acid, trifluoromethanesulphonic acid, perfluorobutanesulphonic acid, benzenesulphonic acid, benzene-1,3-disulphonic acid, toluenesulphonic acid, ethane-1,2-di-sulphonic acid, butane-1,4-di-sulphonic acid, benzylsulphonic acid, 4-(2-dodecyl)-phenylsulphonic acid and hexadecyl- and octadecyl-sulphonic acid.

Acyl radicals (Y) of an aliphatic carboxylic acid with a pK value greater than 1 which may be mentioned are radicals of the formula

wherein:
$R^7$ represents an alkyl radical with 1 to 4 carbon atoms which is optionally substituted by fluorine and chlorine.

Examples of carboxylic acids which may be mentioned are: dichloroacetic acid, trichloroacetic acid, perchloropropionic acid and trifluoroacetic acid.

The following acids may be mentioned as examples of acids which are particularly preferred for the process according to the invention: trichloroacetic acid and trifluoroacetic acid.

One can carry out the process according to the invention in the presence of one or more acids.

Components which may be mentioned as the component which forms carbonium ion, for the process according to the invention, are those which are known to be activated with acids, according to the Ritter reaction, to give a carboniumion. Examples of these components are secondary or tertiary aliphatic alcohols, esters and olefins.

Secondary and tertiary alcohols which may be mentioned are compounds of the formula

wherein:
$R^8$ denotes hydrogen, alkyl, aralkyl or aryl and
$R^9$ and $R^{10}$ are identical or different and denote alkyl or aralkyl.

Esters which may be mentioned are compounds of the formula

wherein:
$R^8$, $R^9$ and $R^{10}$ have the abovementioned meaning and
$R^{11}$ denotes an acyl radical of an inorganic or organic acid.

Olefins which may be mentioned are compounds of the formula

wherein:
$R^{12}$, $R^{13}$ and $R^{14}$ are identical or different and denote hydrogen, alkyl, aralkyl or aryl and
$R^{15}$ denotes alkyl, aralkyl or aryl.

It is also possible for in each case two of the radicals $R^{12}$ to $R^{15}$ to be bonded to form cyclo-aliphatic or aromatic, carbocyclic rings.

Nitriles for the process according to the invention which may be mentioned are compounds of the formula

wherein:
$R^{16}$ denotes hydrogen, alkyl, alkenyl, aralkyl or aryl.

Alkyl radicals ($R^8$ to $R^{10}$ and $R^{12}$ to $R^{16}$) can be, for example, straight-chain or branched hydrocarbon radicals with 1 to 12 carbon atoms. Preferred radicals which may be mentioned are: methyl, ethyl, propyl, isopropyl, butyl, isobutyl, pentyl, isopentyl, hexyl and isohexyl.

Aralkyl radicals ($R^8$ to $R^{10}$ and $R^{12}$ to $R^{16}$) can have a straight-chain or branched hydrocarbon radical with up to 6, preferably with up to 3, carbon atoms in the aliphatic part and a radical from the benzene series, preferably phenyl and naphthyl, in the aromatic part. Examples which may be mentioned are: benzyl, phenethyl, benzhydryl and phenyl-dimethyl-methyl.

Aryl radicals ($R^8$ and $R^{12}$ to $R^{16}$) can be aromatic carbocyclic radicals with 5 to 8 carbon atoms, such as phenyl, naphthyl and diphenyl, preferably phenyl.

Alkenyl radicals ($R^{16}$) can be vinyl, propenyl and cyclopropenyl.

Examples of acyl radicals ($R^{11}$) which may be mentioned are the sulphate, phosphate, acetate, trichloroacetate and trifluoroacetate radical.

The preparation of the individual components for the process according to the invention is known. In detail, the following compounds may be mentioned as examples:

As alcohols: isopropanol, tert.-butanol, sec.-butanol, iso-amyl alcohol, cyclohexanol, benzyl alcohol, borneol, terpineol and menthol.

As esters: sulphuric acid monoesters of isopropanol and cyclohexanol and the trifluoroacetates which are formed in the addition of trifluoroacetic acid onto mono-olefines and di-olefines, such as propene, isobutene, cyclopenta-1,5-diene and dicyclopentadiene.

As olefins: propene, isobutene, but-1-ene, cis- and trans-but-2-ene, 2-methyl-but-2-ene, diisobutene, triisobutene, tetraisobutene, tri- and tetra-propene, α- and β-pinene, styrene, α-methyl-styrene, cyclohexene, 1-methyl-cyclohexene, isoprene, dicyclopentadiene, 2,5-dimethylhexa-1,5-diene, limonene, methallyl chloride, methallyl cyanide, 3-cyclohexene-1-carboxylic acid nitrile, 4-methylcyclohexene-1-carboxylic acid nitrile, 3-cyclohexene-1-carboxylic acid methyl ester, 3-cyclohexene-1-carboxylic acid ethyl ester, 3-cyclohexene-1-carboxylic acid butyl ester and abietic acid methyl ester, cyclopentene.

As nitriles: hydrocyanic acid, acetonitrile, acrylonitrile, propionitrile, pivalonitrile, lauric acid nitrile, stearic acid nitrile, benzyl cyanide and benzonitrile.

In general, the process according to the invention is carried out in the temperature range from about 0° C. to about 120° C., preferably from 10° C. to 100° C. and particularly preferably from 25° to 90° C. In the case of temperatures above 60° C., it can be advantageous to carry out the reaction under pressure in order to keep unreacted or excess, low-boiling reactants, such as, for example, hydrocyanic acid, in the liquid reaction phase.

In order to achieve high space/time yields, it can be appropriate to employ the nitrile in an at least stoichiometric amount, relative to the component which forms carbonium ions; an excess of nitrile over components which form carbonium ions of up to 10:1 can advantageously be employed, and in general it is advisable to employ the nitrile in a molar ratio of from 1 to 3, relative to the components which form carbonium ions. Favourable space/time yields are furthermore obtained when the molar amount of the acid reaches at least the value of the sum of the molar amounts of the component which forms carbonium ions and carboxylic acid amide already present in the reaction medium, e.g. from recycling the acid containing residual amide out of former run. An excess of the acid above this value increases the rate of reaction. In general, it is advisable to employ the acid in the ratio of from 1 to 3, relative to the sum of the component which forms carbonium ions and the carboxylic acid amide.

In a particular embodiment of the process according to the invention, catalytic amounts of perfluoroalkanesulphonic acids, such as perfluorobutane- or perfluorooctane-sulphonic acid, or perfluoroalkanecarboxylic acids, such as trifluoroacetic acid, are added to the reaction in order to increase the rate of reaction. In general, the amounts added are between 1 and 10 mol % of the total amount of acid.

The distillation in the process according to the invention can be carried out in the customary manner. It can be carried out, for example, in the following distillation equipment: thin film evaporator, falling film evaporator and spiral tube evaporator.

In general, the distillation in the process according to the invention can be carried out at distillation bottom temperatures of 90° to 180° C., preferably of 100° to 150° C., and under a pressure of 0.1 mbar to 1 bar, preferably of 0.1 mbar to 100 mbars.

In the process according to the invention, the N-alkyl-substituted carboxylic acid amide and the acid are obtained after the distillation. A mixture of carboxylic acid amide and acid which is obtained in some cases can be optionally partially recycled into the reaction again.

The process according to the invention can be carried out either discontinuously or continuously.

The process according to the invention can be carried out as follows:

The component which forms carbonium ions and the nitrile are fed to a reactor, for example a kettle provided with cooling and stirring devices or a cascade of kettles, in which a mixture of the employed acid and, if appropriate, the reaction product are present.

In the case where the boiling point of the carboxylic acid amide is lower than that of the acid, the reaction mixture is fed, after the reaction, to a distillation apparatus which appropriately operates continuously, preferably a thin film evaporator, a falling film evaporator or a spiral tube evaporator, and, depending on the reaction conditions (for example temperature, pressure, evaporator surface and residence time), some or all of the carboxylic acid amide is separated off. The distillation sump containing the acid according to the invention and residual carboxylic acid amide, can, of course, be separated completely by further distillation. However, it is also possible, especially in the case of a continuous procedure, to recycle some or all of the distillation bottom material to the reaction. In order to keep the proportion of by-products low, 0.1 to 5% of the distillation bottom material is advantageously separated off, and this part is appropriately fed to a separate working up process, for example a residue combustion.

In the case where the boiling point of the acid is lower than that of the carboxylic acid amide, it can be appropriate to separate the acid from the carboxylic acid amide which remains by carrier gas or carrier vapour distillation. Examples of carrier gases which can be used here are inert gases, such as helium, argon and nitrogen, the nitriles employed, such as hydrocyanic acid, acetonitrile and acrylonitrile, can be used as the carrier vapour. One can for example use chlorohydrocarbons, such as chlorobenzene and dichlorobenzene, for a carrier vapour distillation.

It was not to be expected that the mixture obtained in the reaction can be worked up by distillation, since decomposition of the reaction product was expected under these conditions. Such a decomposition occurs, for example, in the case of sulphuric acid, which is particularly frequently used as the reaction medium for the Ritter reaction (German Auslegeschrift (DAS) 2,144,230, column 1, line 41 to column 2, line 20). This difficulty makes it necessary to treat the reaction product, for example with a large excess of water.

An extraction step, without which, according to DAS 2,144,230, working up by distillation is impossible, is also advantageously spared by the process according to the invention.

The process according to the invention has the advantage that no waste acids or waste salts are obtained during the isolation of the reaction product. It can therefore be carried out advantageously and without pollution of the environment.

The N-substituted carboxylic acid amides which can be prepared by the process according to the invention can be employed as printing auxiliaries or in the preparation of textile auxiliaries or can be converted into amines.

EXAMPLE 1

222 g of tert.-butanol are metered into a solution of 150 g of hydrocyanic acid in 420 g of methanesulphonic acid, which is in a stirred vessel provided with a reflux condenser and dropping funnel, in the course of one hour, whilst stirring and cooling. The reaction temperature is kept between 20° and 40° C., rising slowly, during the dropwise addition. The reaction mixture is kept at 40° C. for 4 hours. Excess hydrocyanic acid is then distilled off in vacuo. The reaction mixture which remains is metered into a thin film evaporator at a wall temperature of the evaporator of 110° to 115° C. 55 g of a mixture of 96% of tert.-butylformamide and 4% of tert.-butanol (determined by gas chromatography) are thereby distilled off and 665 g of a bottom product consisting of methanesulphonic acid and tert.-butylformamide in the ratio 64:36 (according to the nuclear magnetic resonance spectrum) are obtained.

EXAMPLE 2

A solution of 150 g of tert.-butanol in 159 g of acrylonitrile are added dropwise to 200 g of methanesulphonic acid, which contains 1 g of phenothiazine as a polymerization inhibitor, in the course of one hour at a reaction temperature of 30° to 35° C. The reaction mixture remains in the reaction vessel at this temperature for 6 hours and, after distilling off excess acrylonitrile, is mixed with 900 g of ethanol and metered into a spiral tube evaporator. 100 g of N-tert.-butylacrylamide distil off with the alcohol at 150° C. and under 25 bars and are isolated by distilling off the ethanol, melting point 125° C. The bottom product can be recycled to the reaction stage with the same result in the yield.

EXAMPLES 3–23

The bottom product obtained in each case as in Example 1 (36% of tert.-butylformamide and 64% of methanesulphonic acid) is reacted with hydrocyanic acid and tert.-butanol and worked up, according to Example 1. The table gives the products employed and the products obtained:

| Example No. | Bottom product employed (g) | % of tert.-butylformamide | % of methanesulphonic acid+ | Starting materials Hydrocyanic acid (g) | tert.-butanol (g) | Yield Tert.-butylformamide (g) | (%) |
|---|---|---|---|---|---|---|---|
| 3 | 665 | 36 | 64 | 121.5 | 150 | 204 | 98 |
| 4 | 653 | 35 | 65 | 119.0 | 147 | 205 | 97 |
| 5 | 640 | 33 | 67 | 117.0 | 144 | 200 | 97 |
| 6 | 628 | 33 | 67 | 115.0 | 141 | 190 | 95 |
| 7 | 610 | 35 | 65 | 111.4 | 138 | 175 | 96 |
| 8 | 603 | 34 | 66 | 110.0 | 136 | 175 | 97 |
| 9 | 590 | 34 | 66 | 108.0 | 133 | 170 | 95 |
| 10 | 581 | 36 | 64 | 106.0 | 131 | 164 | 98 |
| 11 | 568 | 34 | 66 | 103.0 | 128 | 170 | 96 |
| 12 | 557 | 33 | 67 | 102.0 | 126 | 174 | 98 |
| 13 | 549 | 34 | 66 | 100.0 | 124 | 158 | 93 |
| 14 | 535 | 36 | 64 | 98.0 | 121 | 150 | 95 |
| 15 | 519 | 33 | 67 | 95.0 | 117 | 155 | 94 |
| 16 | 505 | 34 | 66 | 92.0 | 114 | 150 | 96 |
| 17 | 492++ | 33 | 67 | 90.0 | 111 | 150 | 94 |
| 18 | 480 | 34 | 66 | 88.0 | 108 | 138 | 95 |
| 19 | 460 | 33 | 67 | 84.0 | 104 | 140 | 96 |
| 20 | 443 | 33 | 67 | 81.0 | 100 | 134 | 96 |
| 21 | 428 | 34 | 66 | 78.0 | 97 | 125 | 93 |
| 22 | 413 | 36 | 64 | 75.5 | 93 | 115 | 94 |
| 23 | 398 | 35 | 65 | 73.0 | 90 | 120 | 94 |

+ Evaluation of the nuclear magnetic resonance spectrum
++ Small amounts of salt

EXAMPLE 24

44 g of tert.-butanol are added dropwise to a mixture of 90 g of trifluoroacetic acid and 185 g of benzyl cyanide at 20° C. in the course of one hour. The reaction mixture is then kept at 60° C. for 6 hours. Most of the trifluoroacetic acid is then distilled off under normal pressure and a small proportion of distilled off under reduced pressure, mixed with excess benzyl cyanide (boiling range up to 75° C./0.5 mm Hg). The distillation bottom product consists of almost pure N-tert.-butyl-phenyl-acetamide.

Melting point 114° C. (recrystallized from alcohol), yield 69 g.

EXAMPLE 25

100 g of tert.-butanol are added dropwise to a mixture of 163 g of trichloroacetic acid and 54 g of adipodinitrile at 80° C. in the course of one hour. The reaction mixture is kept at 80° C. for 7 hours. Thereafter, the reaction product is separated off by vacuum distillation of the trichloroacetic acid employed, which is distilled off at about 100° C./13 mm Hg. 90 g of adipic acid N-tert.-butyl-diamide are obtained, which remain as a solid residue in the reaction vessel.

Melting point 213° to 215° C. (recrystallized from ethanol).

EXAMPLE 26

84 g of acrylonitrile are added dropwise to a solution of 1 g of phenothiazine in 90 g of trifluoroacetic acid at 20° C., whilst stirring. Thereafter, 43 g of tert.-butanol are added dropwise at 35° C. The reaction mixture is kept at 60° to 70° C. for 6 hours and then worked up by distillation. Acrylonitrile, trifluoroacetic acid and some of the N-tert.-butylacrylamide formed are distilled off under reduced pressure. 36 g of N-tert.-butylacrylamide (melting point 120° to 122° C.) remain as the distillation bottom product. The distillate can be re-used in the reaction with the same result.

EXAMPLE 27

126 g of tripropene are added dropwise to a solution of 18 g of water in 170 g of trifluoroacetic acid at room temperature, the stirred mixture is warmed to 65° C. and 40 g of hydrocyanic acid are metered in in the course of 45 minutes. The reaction mixture is kept at 60° to 65° C. for one hour and then worked up by distillation under a pressure of 12 to 15 mm Hg, the distillation bottom temperature being increased from room temperature up to 149° C. The trifluoroacetic acid employed and excess hydrocyanic acid and small amounts of N-i-nonylformamide are obtained in this manner as a distillate with a boiling range of <30° C.–139° C./15 mm Hg, which can be re-used in the reaction, and then 146 g of pure N-i-nonyl-formamide with a boiling range of 142° to 146° C./13 mm Hg are obtained.

EXAMPLE 28

55 g of tert.-butanol are added dropwise to a mixture of 140 g of polyphosphoric acid (76% of $P_2O_5$) and 82 g of acetonitrile, which are initially introduced into a reaction vessel provided with a stirrer, dropping funnel and reflux condenser, at 50°–55° C. The reaction mixture is kept at 55°–60° C. for 3 hours and then metered into a thin film evaporator. 77 g of distillate are obtained and are then fractionated, 47 g of acetonitrile and 30 g of tert.-butylacetamide (boiling point 99°–100° C., melting point 93°–94° C.) being obtained. The bottom product (185 g) obtained during the thin film distillation contains 27% of tert.-butylacetamide, in addition to the polyphosphoric acid employed (determined by nuclear magnetic resonance spectroscopy). The bottom product can be re-used in the reaction with the same result in the yield.

EXAMPLE 29

A stirred mixture of 880 g of a $C_{12}$-alkyl-benzenesulphonic acid and 130 ml of hydrocyanic acid is warmed to 50° C., whilst cooling under reflux. 181 g of tert.-butanol and 70 ml of hydrocyanic acid are added dropwise to this mixture. The hydrocyanic acid excess is distilled off in vacuo after 1.5 hours. The reaction mixture is subjected to thin film distillation at an evaporator temperature of 135° C. and under a pressure of 0.5 mm Hg. 101 g of tert.-butylformamide and 950 g of a distillation bottom product which is re-used in the reaction are obtained. 80 ml of hydrocyanic acid are reacted with 75 g of tert.-butanol in this bottom product under the reaction conditions indicated above. The subsequent thin film distillation gives 110 g of tert.-butylformamide.

EXAMPLE 30

259 g of tert.-butanol are added dropwise to a mixture of 435 g of sulphuric acid mono-n-butyl ester and 180 ml of hydrocyanic acid at 30°–40° C. and the reaction is brought to completion at 40° C. in the course of 3 hours. The reaction mixture is subjected to thin film distillation. 90 g of a distillate which consists of a mixture of tert.-butylformamide, n-butanol and n-butyl formate are obtained at an evaporator temperature of 115° C. and under a pressure of 0.5 mm Hg.

The distillation bottom product contains 35% of tert.-butylformamide. It is reacted again with 75 g of tert.-butanol and 80 ml of HCN under the conditions indicated. 64 g (94% pure) of tert.-butylformamide and 555 of distillation bottom material, which was employed in the reaction with the same result, are obtained by subsequent thin film distillation (as indicated above).

EXAMPLE 31

660 g of p-dodecylbenzenesulphonic acid are initially introduced into a stirred vessel provided with a thermometer, dropping funnel, reflux condenser and drying tube. 160 ml of hydrocyanic acid are added at 20°–25° C. As soon as the hydrocyanic acid has been stirred in thoroughly, the mixture is warmed to 30° to 35° C. and 148 g of tert.-butanol are added dropwise in the course of 30 minutes. The temperature is kept at 40°–42° C. by cooling slightly. The mixture is subsequently stirred at this temperature for a further 3 hours and unreacted hydrocyanic acid is then distilled off in vacuo. 75–80 ml of hydrocyanic acid are recovered.

The residue which remains is fed into a thin film evaporator at a wall temperature of 145° C. 106 g of a mixture consisting of 94% of tert.-butylformamide and 6% of tert.-butanol (determined by gas chromatography) thereby distil off. 750 g of bottom product are obtained, which contain sulphonic acid and tert.-butylformamide in the ratio 2:1 (according to nuclear magnetic resonance spectroscopy).

The bottom product can be re-used with the same result.

What is claimed is:

1. In a process for the preparation of N-alkyl-substituted carboxylic acid amides by contacting a component which forms a carbonium ion with nitrile in the presence of an unneutralized acid, the improvement which comprises employing as the acid an acid of the formula HY wherein Y represents

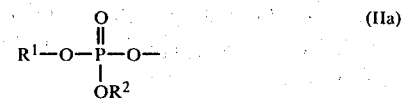

wherein:
R$^1$ and R$^2$ are identical or different and represent hydrogen or an alkyl radical with 1 to 12 carbon atoms; or

wherein:
R$^1$ represents an alkyl radical with 1 to 12 carbon atoms or,
Y represents

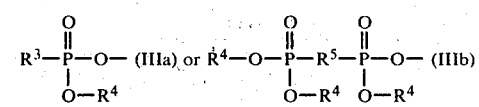

wherein
R$^3$ represents a straight-chain or branched alkyl or alkenyl radical, aryl, or aralkyl,
R$^4$ represents hydrogen or a straight or branched alkyl radical, and
R$^5$ represents an alkylene radical, which is optionally substituted by C$_1$ to C$_4$ alkyl, or an arylene radical; or Y represents R$^6$—SO$_3$— wherein
R$^6$ represents an alkyl radical or aralkyl radical, which is optionally substituted by fluorine or chlorine, or an aryl radical, which is optionally substituted by fluorine, chlorine, C$_1$–C$_4$-alkyl or a sulphonic acid group, and separating the resultant reaction mixture by distillation.

2. A process according to claim 1 wherein the molar amount of acid employed is at least the value of the sum of the molar amount of carboxylic acid amide already present in the reaction mixture and of the component which forms carbonium ions.

3. A process according to claim 1 wherein Y has the formula

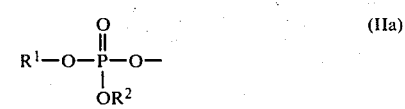

wherein:
R$^1$ and R$^2$ are identical or different and represent hydrogen or alkyl with 1 to 12 carbon atoms.

4. A process according to claim 1 wherein Y has the formula

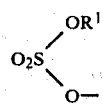 (IIb)

wherein:
R$^1$ is an alkyl radical with 1 to 12 carbon atoms.

5. A process according to claim 1 wherein said Y has the formula

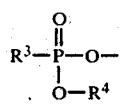 (IIIa)

wherein:
R$^3$ represents a straight-chain or branched alkyl or alkenyl radical, aryl or aralkyl and
R$^4$ represents hydrogen or a straight-chain or branched alkyl radical.

6. A process according to claim 1 wherein said Y has the formula

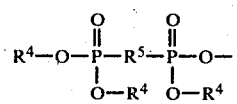 (IIIb)

wherein:
R$^4$ represents hydrogen or a straight-chain or branched alkyl radical, which is optionally substituted by C$_1$ to C$_4$-alkyl, or an arylene radical.

7. A process according to claim 1 wherein said Y has the formula

R$^6$—SO$_3$— (IV)

wherein:
R$^6$ represents an alkyl radical or aralkyl radical, which is optionally subsituted by fluorine or chlorine, or an aryl radical, which is optionally substituted by fluorine, chlorine, C$_1$-C$_4$-alkyl or a sulphonic acid group.

8. A process according to claim 1 wherein said component which forms a carbonium ion is secondary or tertiary aliphatic alcohol, ester or olefin.

9. A process according to claim 1 wherein said component which forms a carbonium ion is a secondary or tertiary alcohol of the formula

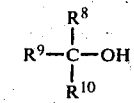 (VI)

wherein:
R$^8$ denotes hydrogen alkyl, aralkyl or aryl and
R$^9$ and R$^{10}$ independently denote alkyl or aralkyl.

10. A process according to claim 1 wherein said component which forms a carbonium ion is an ester of the formula

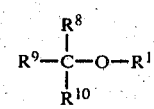 (VII)

wherein:
R$^8$ denotes hydrogen, alkyl, aralkyl, or aryl;
R$^9$ and R$^{10}$ independently denote aklyl or aralkyl; and
R$^{11}$ denotes an acyl radical of an inorganic or organic acid.

11. A process according to claim 1 wherein said component which forms a carbonium ion is an olefin of the formula

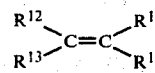 (VIII)

wherein:
R$^{12}$, R$^{13}$, and R$^{14}$ independently represent hydrogen alkyl, aralkyl or aryl and
R$^{15}$ denotes alkyl, aralkyl or aryl.

12. A process according to claim 1 wherein said nitrile has the formula

R$^{16}$—CN (IX)

wherein:
R$^{16}$ denotes hydrogen alkyl, alkenyl, aralkyl or aryl.

13. A process according claim 1 wherein said acid contains catalytic amounts of a perfluoroalkanesulphonic acid or perfluoroalkanecarboxylic acid.

14. A process according to claim 1, wherein 0.1 to 5 percent of the distillation of bottom material is separated off in order to keep the proportion of by-products low.

15. A process according to claim 1, wherein a mixture of carboxylic acid amide and acid are distilled over and a portion of the same are recycled to the reaction.

16. A process according to claim 1 wherein following distillation, the distillation sump product containing acid and residual carboxylic acid amide are subjected to further distillation to separate the same.

17. A process according to claim 1 wherein at least a portion of the distillation bottom material is recycled to the reaction.

* * * * *